(12) United States Patent
Popp et al.

(10) Patent No.: US 6,846,374 B2
(45) Date of Patent: Jan. 25, 2005

(54) METHOD AND APPARATUS FOR MAKING PREFASTENED AND REFASTENABLE PANT WITH DESIRED WAIST AND HIP FIT

(75) Inventors: Robert Lee Popp, Hortonville, WI (US); Joseph Daniel Coenen, Neenah, WI (US); David Arthur Kuen, Neenah, WI (US); Christopher Peter Olson, Neenah, WI (US); Shawn Ahmed Quereshi, Neenah, WI (US)

(73) Assignee: Kimberly-Clark Worldwide, Neenah, WI (US)

( * ) Notice: Subject to any disclaimer, the term of this patent is extended or adjusted under 35 U.S.C. 154(b) by 291 days.

(21) Appl. No.: 09/827,192

(22) Filed: Apr. 5, 2001

(65) Prior Publication Data

US 2002/0173767 A1 Nov. 21, 2002

Related U.S. Application Data

(60) Provisional application No. 60/204,495, filed on May 16, 2000.

(51) Int. Cl.⁷ .......................... A61F 13/15; B32B 31/00
(52) U.S. Cl. .......................... 156/85; 156/161; 156/163; 156/164; 156/227; 156/229
(58) Field of Search .......................... 156/227, 85, 161, 156/163, 164, 229

(56) References Cited

U.S. PATENT DOCUMENTS

| | | |
|---|---|---|
| 1,912,466 A | 6/1933 | Remington |
| 1,912,724 A | 6/1933 | Remington |
| 2,037,561 A | 4/1936 | Blosser et al. |
| 2,714,230 A | 8/1955 | Young |
| 3,116,920 A | 1/1964 | Geer et al. |
| 3,502,322 A | 3/1970 | Cran |
| 3,632,030 A | 1/1972 | Cohn et al. |
| 3,669,800 A | 6/1972 | Gore |
| 3,808,767 A | 5/1974 | Reid |
| 3,870,292 A | 3/1975 | Bradley |
| 3,874,043 A | 4/1975 | Holm |
| 3,918,706 A | 11/1975 | Craft |
| 3,994,486 A | 11/1976 | Nystrand |
| 4,018,432 A | 4/1977 | Frick |
| 4,025,373 A | 5/1977 | Hirsch et al. |
| 4,053,967 A | 10/1977 | Mair |
| 4,145,763 A | 3/1979 | Abrams et al. |
| 4,170,347 A | 10/1979 | Lewis |
| 4,186,860 A | 2/1980 | Reba |
| 4,197,621 A | 4/1980 | Mair |
| 4,205,679 A | 6/1980 | Repke et al. |
| 4,279,610 A | 7/1981 | Reba |

(List continued on next page.)

FOREIGN PATENT DOCUMENTS

| | | |
|---|---|---|
| EP | 0 217 032 A2 | 4/1987 |
| EP | 0 320 989 A2 | 6/1989 |
| EP | 0 532 486 A1 | 3/1993 |
| EP | 0 631 766 A1 | 1/1995 |
| EP | 0 689 816 A2 | 1/1996 |
| EP | 0 753 292 A2 | 1/1997 |
| EP | 0 761 193 A2 | 3/1997 |
| EP | 0 800 808 A1 | 10/1997 |

(List continued on next page.)

*Primary Examiner*—Jeff H. Aftergut
(74) *Attorney, Agent, or Firm*—Thomas M. Gage; John L. Brodersen

(57) ABSTRACT

A process for making a prefastened and refastenable pant includes providing a plurality of discrete articles having side panels and waist regions including an activatable retractive material. The side panels can be folded parallel to a longitudinal centerline to overlap at least portions of first and second fastening components. The fastening components are then engaged to form a prefastened and refastenable pant. The retractive material can be activated subsequent to engagement of the fastening components, or subsequent to obtaining position control of the side panels, to provide the pant with a waistband-to-hip circumference ratio of about 95 percent or less. The prefastened and refastenable pant and apparatus for its manufacture are also disclosed.

16 Claims, 10 Drawing Sheets

U.S. PATENT DOCUMENTS

| | | | |
|---|---|---|---|
| 4,323,534 A | 4/1982 | DesMarais | |
| 4,342,413 A | 8/1982 | Reba | |
| 4,402,690 A | 9/1983 | Redfern | |
| 4,418,513 A | 12/1983 | Plahm | |
| 4,453,709 A | 6/1984 | Reba | |
| 4,479,640 A | 10/1984 | Smith | |
| 4,516,760 A | 5/1985 | Stumpf | |
| 4,543,154 A | 9/1985 | Reiter | |
| 4,597,573 A | 7/1986 | Reba et al. | |
| 4,610,680 A | 9/1986 | LaFleur | |
| 4,615,695 A | 10/1986 | Cooper | |
| 4,640,726 A | 2/1987 | Sallee et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,680,450 A * | 7/1987 | Thorson et al. | 219/388 |
| 4,699,622 A | 10/1987 | Toussant et al. | |
| 4,702,468 A | 10/1987 | Pollich | |
| 4,704,116 A | 11/1987 | Enloe | |
| 4,710,189 A | 12/1987 | Lash | |
| 4,717,375 A | 1/1988 | Lundmark | |
| 4,750,442 A | 6/1988 | Keeton | |
| 4,808,252 A | 2/1989 | Lash | |
| 4,834,738 A | 5/1989 | Kielpikowski et al. | |
| 4,865,579 A | 9/1989 | Kirby et al. | |
| 4,875,668 A | 10/1989 | Spyra | |
| 4,883,549 A | 11/1989 | Frost et al. | |
| 4,885,853 A | 12/1989 | McCabe | |
| 4,908,247 A * | 3/1990 | Baird et al. | 156/164 |
| 4,936,840 A | 6/1990 | Proxmire | |
| 4,940,464 A | 7/1990 | Van Gompel et al. | |
| 5,046,272 A | 9/1991 | Vogt et al. | |
| 5,087,253 A | 2/1992 | Cooper | |
| 5,092,862 A * | 3/1992 | Muckenfuhs et al. | 604/386 |
| 5,092,863 A | 3/1992 | Schanzlin | |
| 5,093,422 A | 3/1992 | Himes | |
| 5,104,116 A | 4/1992 | Pohjola | |
| 5,110,403 A | 5/1992 | Ehlert | |
| 5,140,757 A | 8/1992 | Terada | |
| 5,176,615 A | 1/1993 | Munsch | |
| 5,184,555 A | 2/1993 | Quadracci et al. | |
| 5,197,722 A | 3/1993 | Adamski, Jr. et al. | |
| 5,199,623 A | 4/1993 | Rajala et al. | |
| 5,224,405 A | 7/1993 | Pohjola | |
| 5,226,992 A | 7/1993 | Morman | |
| 5,300,007 A | 4/1994 | Kober | |
| 5,304,599 A | 4/1994 | Himes | |
| 5,330,598 A | 7/1994 | Erdman et al. | |
| 5,344,691 A | 9/1994 | Hanschen et al. | |
| 5,353,979 A | 10/1994 | Gartmann | |
| 5,363,784 A | 11/1994 | Adamski, Jr. et al. | |
| 5,370,634 A | 12/1994 | Ando et al. | |
| 5,399,219 A | 3/1995 | Roessler et al. | |
| 5,435,802 A | 7/1995 | Kober | |
| 5,556,360 A | 9/1996 | Kober et al. | |
| 5,607,416 A * | 3/1997 | Yamamoto et al. | 604/397 |
| 5,626,711 A * | 5/1997 | Herrmann | 156/496 |
| 5,660,666 A | 8/1997 | Dilnik et al. | |
| 5,669,996 A * | 9/1997 | Jessup | 156/163 |
| 5,705,013 A | 1/1998 | Nease et al. | |
| 5,765,495 A | 6/1998 | Adamski, Jr. | |
| 5,766,389 A | 6/1998 | Brandon et al. | |
| 5,772,825 A * | 6/1998 | Schmitz | 156/164 |
| 5,779,831 A | 7/1998 | Schmitz | |
| 5,785,699 A | 7/1998 | Schmitz | |
| 5,788,805 A | 8/1998 | Herrmann | |
| 5,795,350 A | 8/1998 | Schmitz | |
| 5,795,433 A | 8/1998 | Niedermeyer | |
| 5,803,448 A | 9/1998 | Stiel et al. | |
| 5,807,368 A | 9/1998 | Helmer | |
| 5,830,206 A | 11/1998 | Larsson | |
| 5,855,574 A * | 1/1999 | Kling et al. | 604/392 |
| 5,858,515 A | 1/1999 | Stokes et al. | |
| 5,865,135 A | 2/1999 | Price et al. | |
| 5,897,545 A | 4/1999 | Kline et al. | |
| 5,904,802 A | 5/1999 | Niedermeyer | |
| 5,915,319 A | 6/1999 | Price et al. | |
| 5,916,203 A | 6/1999 | Brandon et al. | |
| 5,919,334 A | 7/1999 | Niedermeyer | |
| 5,997,981 A | 12/1999 | McCormack et al. | |
| 6,022,431 A | 2/2000 | Blenke et al. | |
| 6,022,432 A | 2/2000 | Elsberg et al. | |
| 6,027,440 A | 2/2000 | Roth | |
| 6,036,805 A | 3/2000 | McNichols | |
| 6,113,717 A | 9/2000 | Vogt et al. | |
| 6,240,569 B1 * | 6/2001 | Van Gompel et al. | 2/400 |
| 6,287,287 B1 | 9/2001 | Elsberg | |
| 6,328,725 B2 | 12/2001 | Fernfors | |
| 6,395,115 B1 | 5/2002 | Popp et al. | |
| 6,409,858 B1 | 6/2002 | Popp et al. | |
| 6,432,243 B1 | 8/2002 | Popp et al. | |
| 6,432,248 B1 | 8/2002 | Popp et al. | |
| 6,447,628 B1 | 9/2002 | Couillard et al. | |
| 6,461,344 B1 | 10/2002 | Widlund et al. | |
| 6,481,362 B2 | 11/2002 | Hietpas et al. | |
| 6,497,032 B2 | 12/2002 | Maxton et al. | |
| 6,513,221 B2 | 2/2003 | Vogt et al. | |
| 6,514,187 B2 | 2/2003 | Coenen et al. | |
| 6,562,167 B2 | 5/2003 | Coenen et al. | |
| 6,565,691 B2 | 5/2003 | Tomsovic et al. | |
| 6,596,113 B2 | 7/2003 | Csida et al. | |
| 2002/0002358 A1 | 1/2002 | Durrance et al. | |
| 2002/0003021 A1 | 1/2002 | Maxton et al. | |
| 2002/0003024 A1 | 1/2002 | Vogt et al. | |
| 2003/0066592 A1 | 4/2003 | Maxton et al. | |
| 2003/0075277 A1 | 4/2003 | Vogt et al. | |

FOREIGN PATENT DOCUMENTS

| | | |
|---|---|---|
| EP | 0 803 602 A1 | 10/1997 |
| EP | 0 820 747 A1 | 1/1998 |
| EP | 0 757 550 B1 | 12/1998 |
| EP | 0 934 739 A2 | 8/1999 |
| FR | 2 299 254 | 8/1976 |
| GB | 1 384 622 | 2/1975 |
| GB | 1 520 740 | 8/1978 |
| GB | 1 593 600 | 7/1981 |
| GB | 2 160 817 A | 1/1986 |
| GB | 2 288 314 A | 10/1995 |
| WO | WO 91/19613 A1 | 12/1991 |
| WO | WO 95/18589 A1 | 7/1995 |
| WO | WO 95/18591 A2 | 7/1995 |
| WO | WO 95/27462 A1 | 10/1995 |
| WO | WO 95/32639 A1 | 12/1995 |
| WO | WO 95/33618 A1 | 12/1995 |
| WO | WO 97/23180 A1 | 7/1997 |
| WO | WO 97/24098 A1 | 7/1997 |
| WO | WO 98/15248 A1 | 4/1998 |
| WO | WO 99/65441 A1 | 12/1999 |
| WO | WO 00/23025 A1 | 4/2000 |
| WO | WO 00/35395 A2 | 6/2000 |
| WO | WO 00/35398 A1 | 6/2000 |
| WO | WO 00/37009 A2 | 6/2000 |

* cited by examiner

METHOD AND APPARATUS FOR MAKING PREFASTENED AND REFASTENABLE PANT WITH DESIRED WAIST AND HIP FIT

This application claims the benefit of earlier filed provisional application Ser. No. 60/204,495, filed May 16, 2000.

BACKGROUND OF THE INVENTION

The present invention pertains to processes and apparatus for making garments, and more particularly to processes and apparatus for making prefastened and refastenable pants.

Prefastened and refastenable pants can be employed for many uses such as disposable absorbent garments. Examples of disposable absorbent garments include diapers, training pants or swim pants, feminine care products, adult incontinence products, or the like. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

Prefastened and refastenable disposable absorbent garments can provide advantages over either conventional two-dimensional or three-dimensional products. Two-dimensional products are generally flat and provided in an unfastened configuration, but include fasteners to secure the product about the wearer. Three-dimensional products, in contrast, have closed sides so that the product has a unitary waist opening and two leg openings.

Prefastened and refastenable products can be applied and/or removed either like a conventional diaper or like a conventional training pant. For use as training pants, for example, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied like either a diaper or a pant permits the interior of the product to be easily checked without having to pull the product downward.

Prefastened and refastenable garments present new challenges for high speed manufacturing. The products must incorporate refastenable fasteners that are properly aligned and engaged. Improperly attached or aligned fasteners can lead to many product deficiencies, including machine waste and/or delay, improper fit, fastener delamination during use, fastener disengagement during use, skin irritation, or the like. Moreover, the manufacturing process should desirably be capable of making pants that provide proper fit in the waist and hip regions.

Thus, what is lacking and needed in the art are processes and apparatus for making prefastened disposable absorbent garments with refastenable fasteners, which processes and apparatus permit proper alignment of the fasteners while also yielding a product with desirable fit properties in the waist and hip regions.

SUMMARY OF THE INVENTION

In response to the above-referenced unfulfilled need in the art, new processes and apparatus for making prefastened and refastenable pants have been discovered. The processes and apparatus allow for manufacturing a pant where folding operations are conducted parallel to the longitudinal centerline of the product. This significantly simplifies the manufacture of prefastened and refastenable garments. To obtain desirable fit properties in the waist and hip regions of fully assembled products, the pants are provided with an activatable retractive material. The process and apparatus provide for activation of the retractive material so that retraction occurs subsequent to folding or subsequent to obtaining position control of product side panels which are to be folded.

One embodiment of a process for making a prefastened and refastenable pant includes the steps of: providing a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels; providing an activatable retractive material in at least one of the waist regions; folding each article through the crotch region; folding the opposed side panels parallel to the longitudinal centerline to overlap at least portions of the first and second fastening components; engaging the first and second fastening components; and activating at least a portion of the retractive material causing the retractive material to retract subsequent to engagement of the fastening components.

Another embodiment of a process for making a prefastened and refastenable pant includes the steps of: providing a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels; providing an activatable retractive material in at least one of the waist regions; obtaining position control of the opposed side panels; activating at least a portion of the retractive material causing retraction of the retractive material; folding each article through the crotch region; folding the opposed side panels parallel to the longitudinal centerline to overlap at least portions of the first and second fastening components; engaging the first and second fastening components; and maintaining position control of the opposed side panels until the fastening components are engaged.

One embodiment of an apparatus for making a prefastened and refastenable pant includes: a pant assembly unit adapted to provide a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels, the pant assembly unit further adapted to provide an activatable retractive material in at least one of the waist regions; a product folding mechanism adapted to fold each article through the crotch region; a side panel folding mechanism adapted to fold the opposed side panels parallel to the longitudinal centerline to overlap at least portions of the first and second fastening components; a fastener engaging mechanism adapted to engage the first and second fastening components; and an activating mechanism adapted to activate at least a portion of the retractive material and cause the retractive material to retract subsequent to engagement of the fastening components.

Another embodiment of an apparatus for making a prefastened and refastenable pant includes: a pant assembly unit adapted to provide a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels, the pant assembly unit further adapted to provide an activatable retractive material in at least one of the waist regions; a position control mechanism adapted to obtain position control of the opposed side panels; an activating mechanism adapted to activate at least a portion of the retractive material and cause the retractive material to retract; a product folding mechanism adapted to fold each article through the crotch region; a side panel folding mechanism adapted to fold the opposed side panels parallel to the longitudinal centerline to overlap at least portions of the first and second fastening components; and a fastener engaging mechanism adapted to engage the first and second fastening components; wherein the position control mechanism maintains position control of the opposed side panels until the fastening components are engaged.

The process and apparatus disclosed herein can provide efficient manufacture of pants having a waistband-to-hip circumference ratio (WHCR) at a 70 gram loading that is about 95 percent or less, such as about 70 to about 95 percent, and more particularly about 90 or less, such as about 75 to about 90 percent. The differential in circumferences results from activation and resulting retraction of the retractive material in the waist region, and particularly the waistband. The smaller circumference at the waistband can hold the pant up on the body when worn, especially when the pant is weighted down with water, urine, BM or other substances encountered during use.

The waistband-to-hip circumference ratio (WHCR) of a pant refers to the ratio of the circumference of the pant measured at the waistband (the "waistband circumference") to the circumference of the pant measured at the hip section (the "hip circumference"), measured at a specified loading and expressed as a percentage. The waistband peripherally surrounds the waist opening of the pant and is formed upon joining the front and back waist regions along refastenable seams. The hip section is disposed between the waistband and the leg openings of the pant and is also formed upon joining the front and back waist regions along the refastenable seams. Both the waistband and the hip section include portions of the front and back waist regions.

Hence, in another respect, the invention pertains to a prefastened and refastenable pant including a chassis having a first waist region with opposed side panels, an opposite second waist region, and a crotch region disposed between and interconnecting the waist regions. The chassis defines a longitudinal centerline, and the waist regions together define a waistband and a hip section. The pant also includes at least one first fastening component disposed in the first waist region, and at least one second fastening component disposed in the second waist region and adapted to refastenably engage the first fastening component. A retractive material is disposed in at least the waistband. The pant is folded through the crotch region and folded through the opposed side panels so that portions of the waist regions overlap. The first and second fastening components are engaged with one another to maintain the pant in a prefastened condition. The pant has a waistband-to-hip circumference ratio of about 95 percent or less which results from activation of the retractive material after the fastening components are engaged to one another.

The WHCR can be measured according to the WHCR procedure set forth hereinafter. In particular, the waistband and hip section circumferences can be measured perpendicular to the longitudinal centerline of the pant at a force of 70 grams. Unless specifically noted, reference herein to WHCR means measurements at a force of 70 grams. At significantly higher forces, for example about 2000 grams, the WHCR can be 100 percent so that the product is easy to raise up over the hips. Particularly, the maximum elongation in the waistband can be about the same as the maximum elongation in the hip section to enable the waistband of the pant to slide up over the hips. In a majority of individuals, including children, the hips have a larger circumference than the waist.

Thus, the waistband can desirably retain its ability to expand to the pre-activated circumference. This ability to expand can be provided by extensible and/or elastic elements provided in the waistband or by extensible and/or elastic retractive members. In particular embodiments, the retractive material can provide the ability of the waistband to expand to approximately the pre-activated circumference. The degree of extensibility and/or elasticity of the retractive material will depend upon the material properties of the selected retractive material. For example, some heat shrinkable films may not be able to fully elongate to the pre-activated length without substantially higher tension. It is noteworthy that products that achieve a narrower waistband by having narrower cut of materials in the upper part of the waist region are unlikely to be able to achieve suitable expansion of the waistband. Similarly, products that achieve a narrower waistband by overlapping greater portions of the upper part of the waist region for fastening are unlikely to be able to achieve suitable expansion of the waistband.

The retractive material can comprise any material adapted to retract upon activation, whether immediately upon activation or subsequently thereto. The retractive material can comprise elastomeric or nonelastomeric materials. Suitable nonelastomeric retractive materials can comprise without limitation polyether block amides (PEBAX) or the like, and laminates thereof. Suitable elastomeric retractive materials can comprise without limitation LYCRA® materials, elastomeric materials including latex rubber or synthetic urethanes, or the like, and laminates thereof. In particular embodiments, the retractive material can comprise an elastomeric material having an unstable state relative to some other stable and elastic state. In such embodiments, the retractive material can but need not have elastomeric properties in the unstable state.

The elastomers useful in retractive materials can be selected from the group consisting of elastomeric thermoplastic polymers. The physical structure of the elastomer can be strands, cast or blown film, any non-woven web of fiber of a desired thermoplastic polymer or a combination thereof. Suitable elastomeric thermoplastic polymers include styrene block copolymers such as, for example, those available under the trademark KRATON® from Shell Chemical Company of Houston, Tex. USA. KRATON® block copolymers are available in several different formulations, a number of which are identified in U.S. Pat. Nos. 4,663,220; 4,323,534; 4,834,738; 5,093,422; and 5,304,599 which are incorporated herein by reference.

Other exemplary elastomeric materials that can be used include polyurethane elastomeric materials such as, for example, those available under the trademark PELLATHANE® from Dow Chemical Company of Midland, Mich. USA or under the trademark ESTANE® from B.F. Goodrich & Company of Akron, Ohio USA or under the trademark MORTHANE® from Morton Thiokol Corporation; polyester elastomeric materials such as, for example, those available under the trade designation HYTREL from E.I Dupont de Nemours & Company of Wilmington, Del. USA and those known as ARNITEL® from DSM of Sittard, Holland; and polymers from metallocene-based catalysis which are available under the name ENGAGE® from Dow Chemical Company of Midland, Mich. USA for polyethylene-based polymers and from Exxon Chemical Company of Baytown, Tex. USA under the trade name ACHIEVE® for polypropylene-based polymers and EXACT® and EXCEED® for polyethylene-based polymers.

The retractive materials can be caused to retract or begin to retract by any activation mechanism appropriate for the selected type of retractive material. Suitable activation methods can include without limitation any means of applying energy to the retractive material, such as heating, electromagnetic radiation such as ultraviolet, infrared, microwave, or gamma radiation; compaction or compression of the retractive material; or the like. For particular materials, removal of a compaction or compression force may activate the retraction.

Upon activation the retractive material can be transformed from an unstable state to a stable state by the application of any form of energy or by any other convenient mechanism. The activation mechanism will depend upon the nature of the retractive material. The stable state need not be an absolute state; rather, it is required only that the state following activation be relatively more stable than the state preceding activation and that the state following activation be sufficiently stable for practical use.

In particular embodiments, the retractive material can comprise an elastomeric material which can be elongated from a stable state to an extended and unstable state. The elastomeric material can be temporarily maintained in the extended and unstable state by application of a compaction force. After a period of time measured from the application of the compaction force, or upon application of energy, the elastomeric material will retract from the extended and unstable state to its stable state. For purposes of the present invention, this form of elastomeric material in its extended and unstable state constitutes a retractive material and the compaction force constitutes activation of the retractive material. Examples of such elastomeric materials include without limitation polyether block amides (PEBAX), or the like.

Activation can occur at any point in the process, provided that retraction caused by the activation occurs subsequent to engagement of the fastening components or subsequent to obtaining position control of product side panels which are to be folded. Retraction can occur subsequent to engaging the fastening components without impacting alignment of the fastening components. Retraction can also occur subsequent to obtaining control of product side panels without impacting alignment of the fastening components, provided position control of the opposed side panels is maintained until the fastening components are engaged. Prior to retraction, the unstretched circumferences of the waistband and hip section can be generally equal, which facilitates manufacture and proper engagement of the fastening components.

In particular embodiments, the side panels can be folded and the fastening components are engaged with one another prior to activation and retraction. This allows the side panels to be folded parallel to the longitudinal centerline, which is a relatively easier manufacturing process than folding the product at an angle relative to the longitudinal centerline. Alternatively, the side panels can be folded, the position of the fastening components can be controlled and maintained, the retractive material can be allowed to retract, and the fastening components can be engaged. Still alternatively, the retractive material can be activated prior to folding and/or fastener engagement, provided the retractive material does not retract prior to engagement of the fastening components. In particular embodiments, activation and retraction of the retractive material occurs in a packaging device such as a product stacker. Thus, the fastening components can be engaged before, during, or after activation of the retractive material.

The retractive material can be disposed at any location within the pant provided retraction of the retractive material will facilitate reduction of the waistband circumference. In particular embodiments, the retractive material can be located in the side panels, between the side panels such as on the absorbent chassis, or a combination of the two. The retractive material can function as another element of the pant, such as the outer cover, the side panels, the bodyside liner, an elastic waistband feature, a fastening component, a pant disposal device, another element of the absorbent chassis, or the like.

The retractive material can be disposed in one or both of the waist regions, the waistband alone, or the waistband and either or both of the hip section or the crotch region. Where the retractive material is used in both the waistband and hip section, activation of the retractive material desirably contributes to greater reduction of the waistband circumference than of the hip circumference. This can be accomplished by having a greater amount of retractive material in the waistband, by selectively activating the retractive material in the waistband to a greater extent than the retractive material in the hip section, by orienting the retractive material in the waistband to be more receptive to activation than in the hip section, by using different types of retractive materials with different retractive properties, by reducing retractive ability of an elastomer after activation such as by cutting or compressing, by providing lower resistance to retraction in the waistband than in the hip section as a whole, or the like. Examples of selective heat activation include applying a higher temperature air flow or a greater volume of heated air to the waistband as compared to the hip section. The retractive material can be oriented in a transverse direction within the pant so that retraction causes a reduction of the waistband circumference of the pant. The retractive material can be adapted to retract upon activation in one direction or in two or more directions.

The pant can be folded in half by a variety of mechanisms. Where the side panels are folded subsequent to folding the product in half, it may be desirable to maintain separation of the side panels and separation of the fastening components while the product is folded in half. Throughout the folding process, the waistband and hip circumferences can be equal, that is a WHCR of approximately 100 percent, or could alternatively be unequal. The fastening components can be engaged simultaneously or sequentially with folding of the pant.

The fastening components can comprise separate elements bonded to another component of the pant. Alternatively, the fastening components can comprise a portion of another element of the pant, such as the bodyside liner, the outer cover, separate side panels if employed, or the like. Thus, the fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

A refastenable fastening system allows for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing. Refastenable fastening systems may be used with a wide variety of absorbent and non-absorbent products, including training pants, swim pants, diaper pants, incontinence garments, feminine care products, health care garments, apparel for institutional, industrial and consumer use, or other garments using mechanical or adhesive fasteners.

Absorbent articles are adapted to be worn adjacent to the body of a wearer to absorb and contain various exudates discharged from the body. The absorbent articles are desirably prefastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U.S. patent application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams;" which is incorporated herein by reference. This reference describes various materials and methods for constructing training pants. Training pants can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; which are also incorporated herein by reference.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

Figure 1:
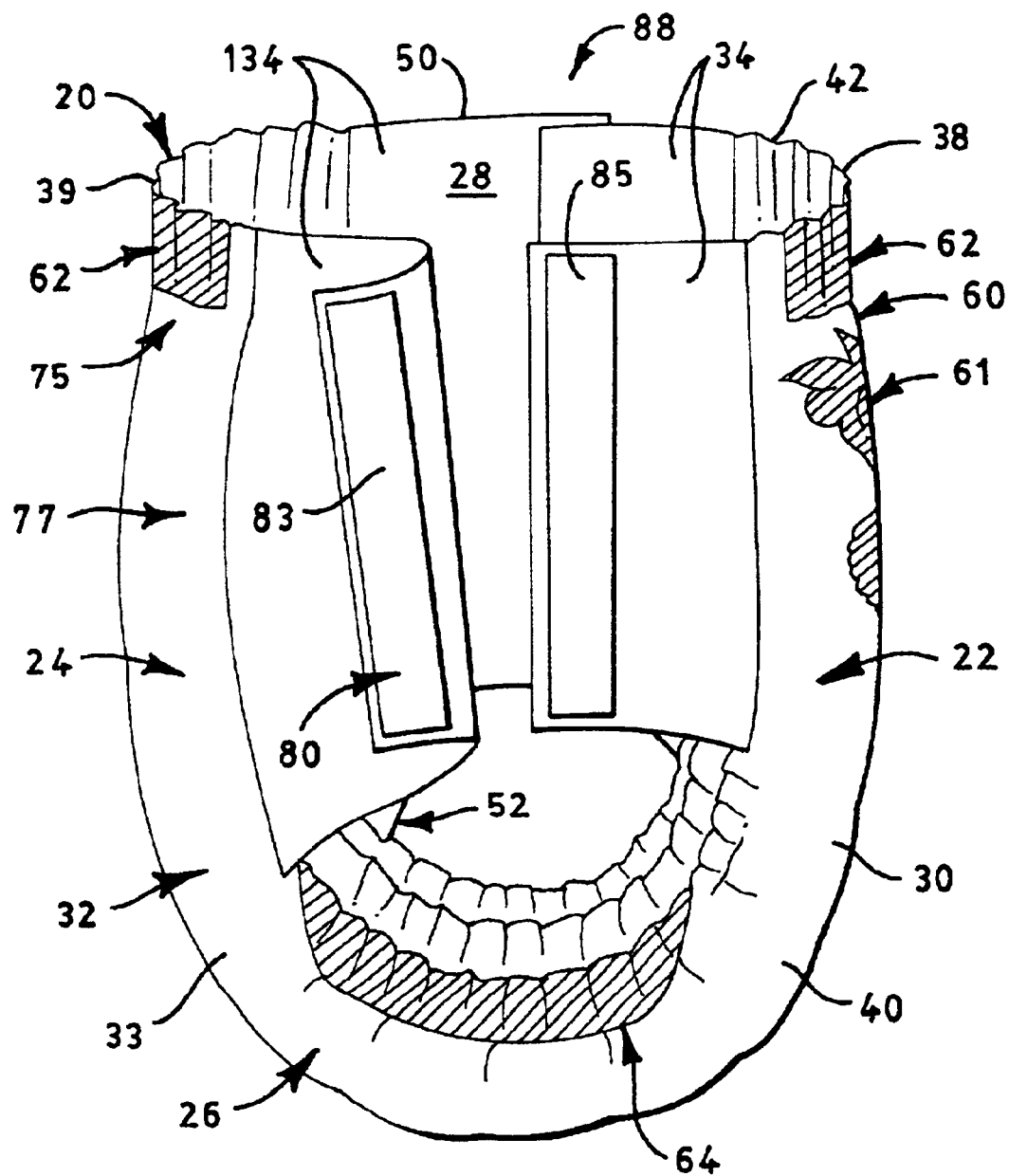
FIG. 1 illustrates a side view of a training pant suitable for use with the process and apparatus according to the present invention, where the fastening system is shown engaged on one side of the training pant and disengaged on the other side of the training pant.

FIG. 1 representatively illustrates one embodiment of training pant 20 in a partially fastened condition. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 2:
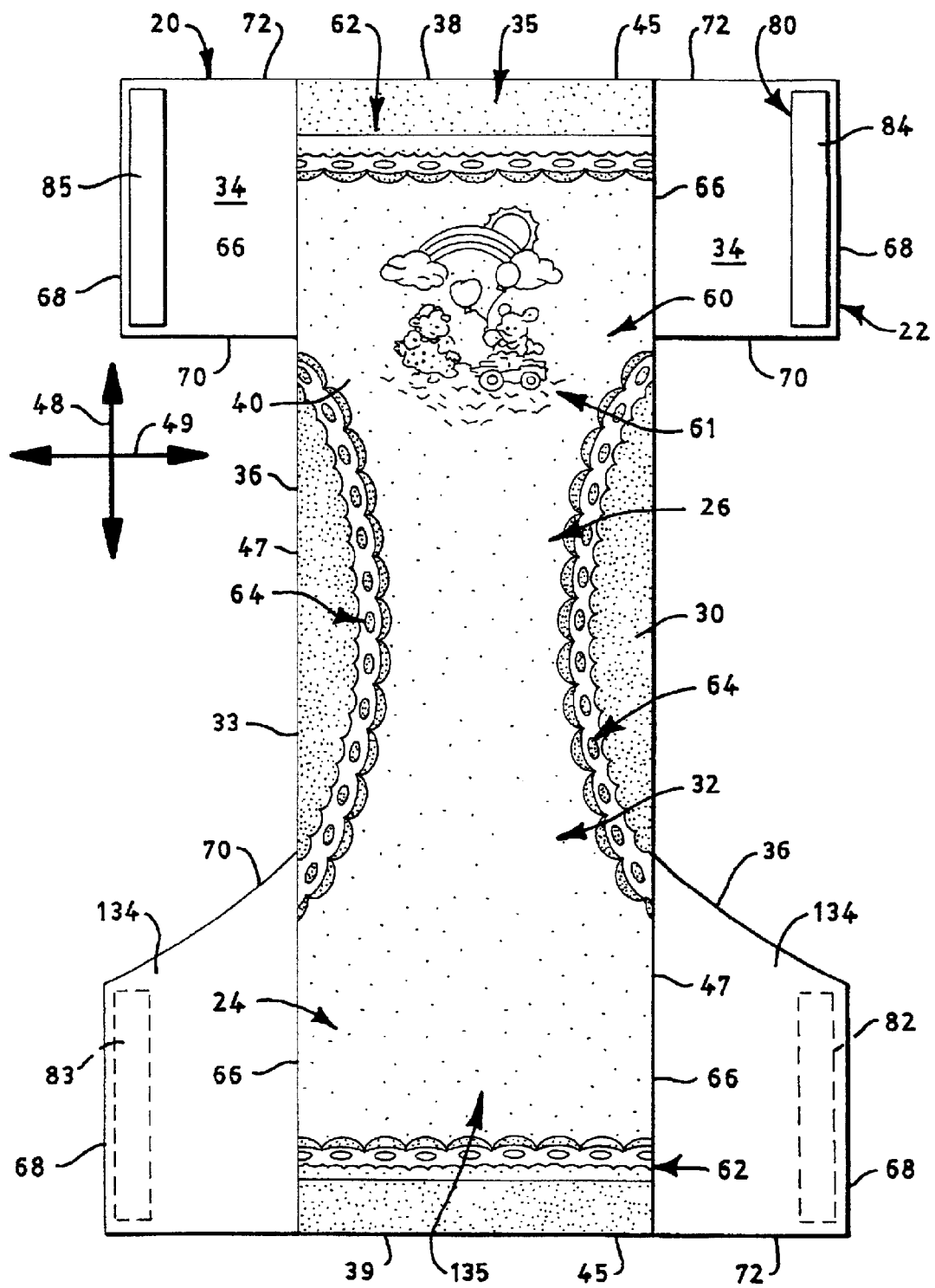
FIG. 2 illustrates a plan view of the training pant shown in FIG. 1 in an unfastened, stretched and laid flat condition, and showing the surface of the training pant that faces away from the wearer.
Figure 3:
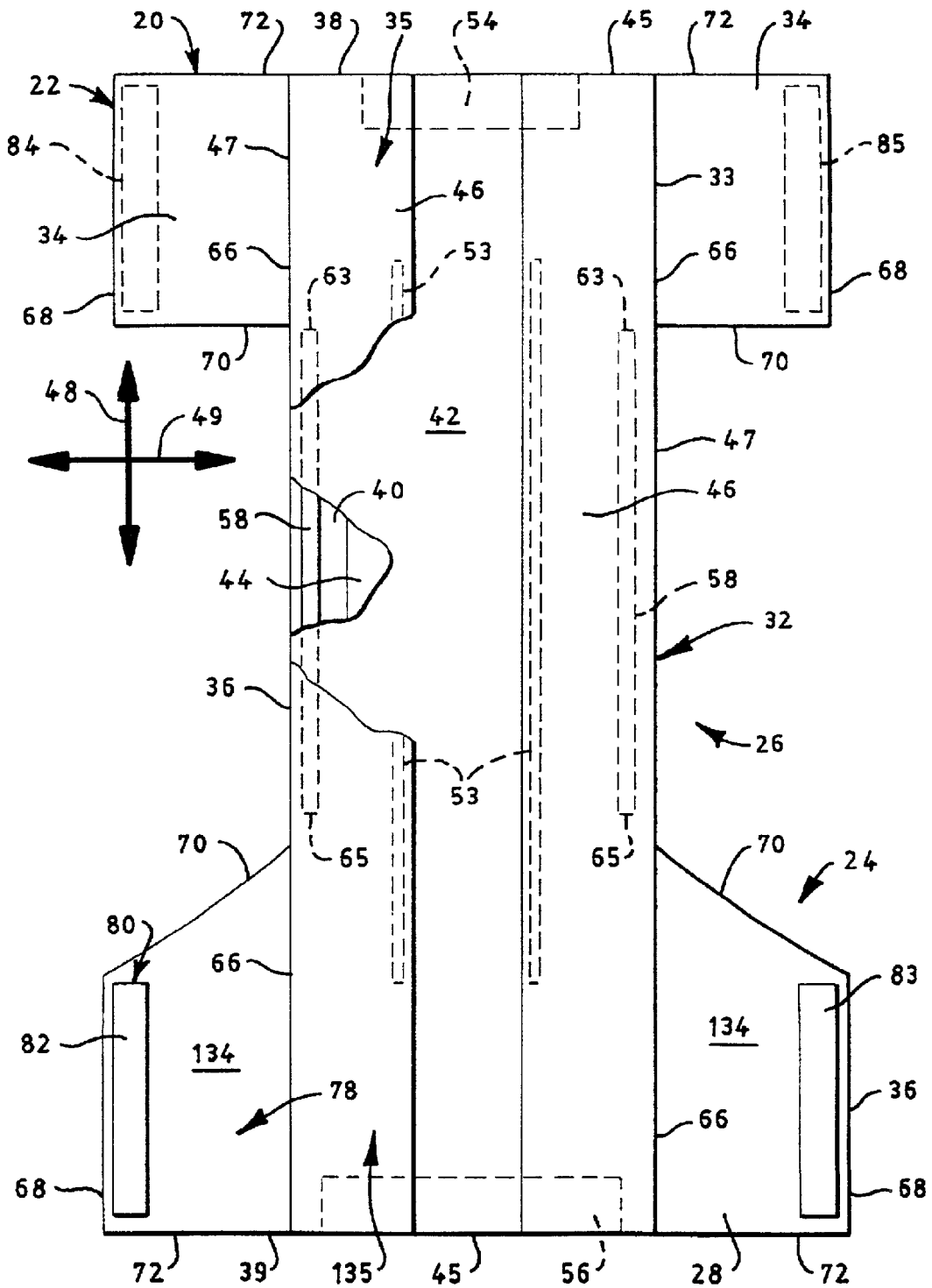
FIG. 3 illustrates a plan view similar to FIG. 2, but showing the surface of the training pant that faces the wearer when the training pant is worn, and with portions cut away to show the underlying features.

The illustrated absorbent chassis 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 2 and 3) positioned between and interconnecting the side panels. The back waist region 24 of the absorbent chassis 32 includes the transversely opposed back side panels 134 and a back center panel 135 (FIGS. 2 and 3) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52. The waist regions 22 and 24 jointly define a waistband 75 (FIGS. 1, 5, 6 and 8–11) that peripherally surrounds the waist opening 50 of the pant 20. The waist regions 22 and 24 also jointly define a hip section 77 (FIGS. 1, 5, 6 and 8–11) that encircles the pant 20 and is disposed between the waistband 75 and the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges, such that the waist elastic members are disposed in the waistband 75 in the fully assembled pant. The leg elastic members 58 are desirably operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

In particular embodiments, the waist elastic members 54 and 56 can be formed of retractive materials. For example, the waist elastic members 54 and 56 can be formed of an elastomeric material that is adapted to retract upon activation by a source of heat.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can comprise elastomeric materials, it can be desirable in some embodiments for the composite structure to be generally inelastic, where the outer cover, the bodyside liner and the absorbent assembly comprise materials that are generally not elastomeric.

The absorbent assembly 44 (FIG. 3) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 2 and 3, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42, or stretchable but inelastic materials.

In particular embodiments, one or more of the side panels 34 and 134 can be formed of retractive materials. For example, the side panels 34 and 134 can be formed of an elastomeric material that is adapted to retract upon activation by a source of heat.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

With particular reference to FIG. 3, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 2, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

The fastening components 82–85 can be adhered to the side panels 34 and 134 by any means known to those skilled in the art such as adhesive bonds, sonic bonds or thermal bonds. In an alternative embodiment, the training pant 20 includes only a single second fastening component disposed in the front waist region 22 for refastenably connecting the first fastening components 82 and 83 (not shown). In a further alternative embodiment, the fastening components can comprise integral portions of the waist regions. For instance, one of the elastomeric front or back side panels can function as second fastening components in that they can comprise a material that is releasably engageable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-with ratio, for example, of about 2 or less, and even about 1 or less.

When the fastening components 82–85 are releasably engaged, the side edges 36 of the absorbent chassis 32 in the crotch region 26 define the leg openings 52, the waist edges 38 and 39 of the absorbent chassis, including the waist end edges 72 of the side panels, define the waist opening 50, and the waist regions 22 and 24 jointly define a waistband 75 and hip section 77. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 1) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal centerlines of the fasteners, measured with the side panels 34 and 134 in an unstretched condition.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Suitable rotary ultrasonic horns are described in U.S. Pat. No. 5,110,403 to Ehlert, which is incorporated herein by reference.

Figure 4:
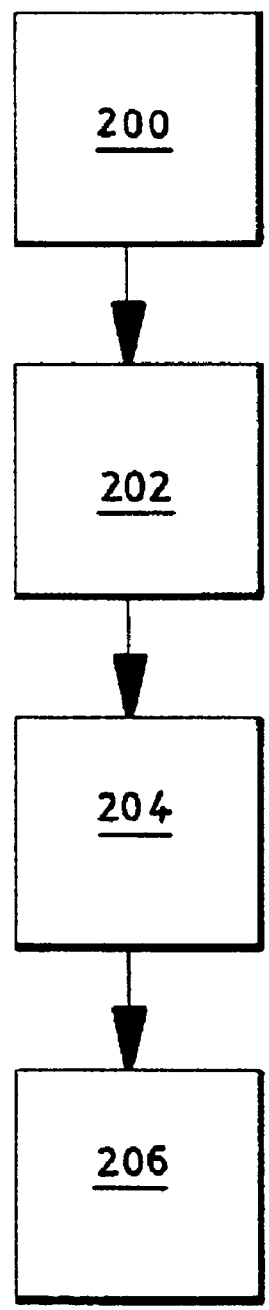
FIG. 4 schematically illustrates a flow diagram for manufacture of one embodiment of a pant according to the present invention.

FIG. 4 schematically illustrates a flow diagram for manufacture of one embodiment of a pant according to the present invention. The components of the pants 20 can be provided and bonded together in an assembly section 200, typically in the form of a continuous web of interconnected and partially assembled pants. The assembly section 200 can include a cutting mechanism which selectively cuts the web into discrete, partially assembled training pants.

The discrete training pants can then be folded at a folding station 202 using any suitable folding mechanism. The training pants 102 can be folded about a fold line generally bisecting the training pants. As such, the waist regions 22 and 24 of each training pant can be positioned in facing relationship with the side panels 34 and 134 extending laterally outward relative to the longitudinal axis 48 of the training pant. The fold line can extend in a lateral direction through the crotch region 26 of the training pant. Desirably, the discrete training pants are consistently folded about the fold line such that the front and back waist edges 38 and 39 of the training pants align with each other.

The opposed side panels 34 and 134 can also be folded in the folding section 202. The side panels 34 and 134 can desirably be folded parallel to the longitudinal centerline of the training pants so that at least portions of the first and second fastening components overlap with one another. The side panels 34 and 134 can alternatively be folded together in conjunction with engagement of the first and second fastening components 82–85 in a seaming section 204. The seaming section 204 forms the refastenable seams 88 of the pants 20. Suitable devices to inwardly fold the side panels 34 and 134 parallel to the longitudinal centerline can include folding boards, folding skis, paddles, fingers, vacuum devices, air blasts, mechanical devices with reciprocating motion such as tuckers, four-bar linkages, slide-crank mechanisms, or the like and combinations thereof.

The training pants 20 can be transported to an activation station 206, which can but need not necessarily follow the seaming section 204 as illustrated. The activation station 206 can comprise an activation source such as a heating unit to instigate retraction of the retractive material. The activation station 206 can comprise a separate stage of the manufacturing operation or can be incorporated into another stage. In particular embodiments, the activation station 206 can be combined with devices such as product stackers for packaging the pants 20. Suitable devices incorporating activation mechanisms are disclosed in U.S. Pat. No. 4,640,726 issued Feb. 3, 1987 to Sallee et al. and U.S. Pat. No. 4,663,106 issued May 5, 1987 to Pomplun et al., which are incorporated herein by reference. In the illustrated embodiment, at least a portion of the retractive material is activated and caused to retract subsequent to engagement of the fastening components 82–85. While the waist elastic members 54 and 56 and side panels 34 and 134 were described as comprising retractive materials, other components of the training pant such as distinct elements or portions of the outer cover, bodyside liner, absorbent assembly or fastening components can alternatively or additionally comprise retractive materials.

In particular embodiments, the retractive material can also be activated prior to engaging the fastening components 82–85. For example, activation can occur prior to folding the side panels 34 and 134 or after folding the side panels but before engaging the fastening components. Such embodiments can include obtaining position control of the side panels and maintaining position control until the fastening components are engaged. The term "position control" as used herein refers to controlling the cross-machine direction position of the fastening components so the fastening components do not move uncontrollably in the cross-machine direction or skew uncontrollably at an angle relative to the machine centerline as a result of activation. Suitable devices for obtaining and maintaining position control can include opposed belts, friction belts, vacuum devices such as conveyors, clamping devices such as tenter frames, pins, clips or chains, or the like and combinations thereof. Carrier strips may be attached to or formed integrally with the pant to assist in maintaining position control, and may be removed from or maintained in the pant as desired. The fastening components can be rotated, inverted or otherwise oriented or positioned prior to engagement.

Figure 5:
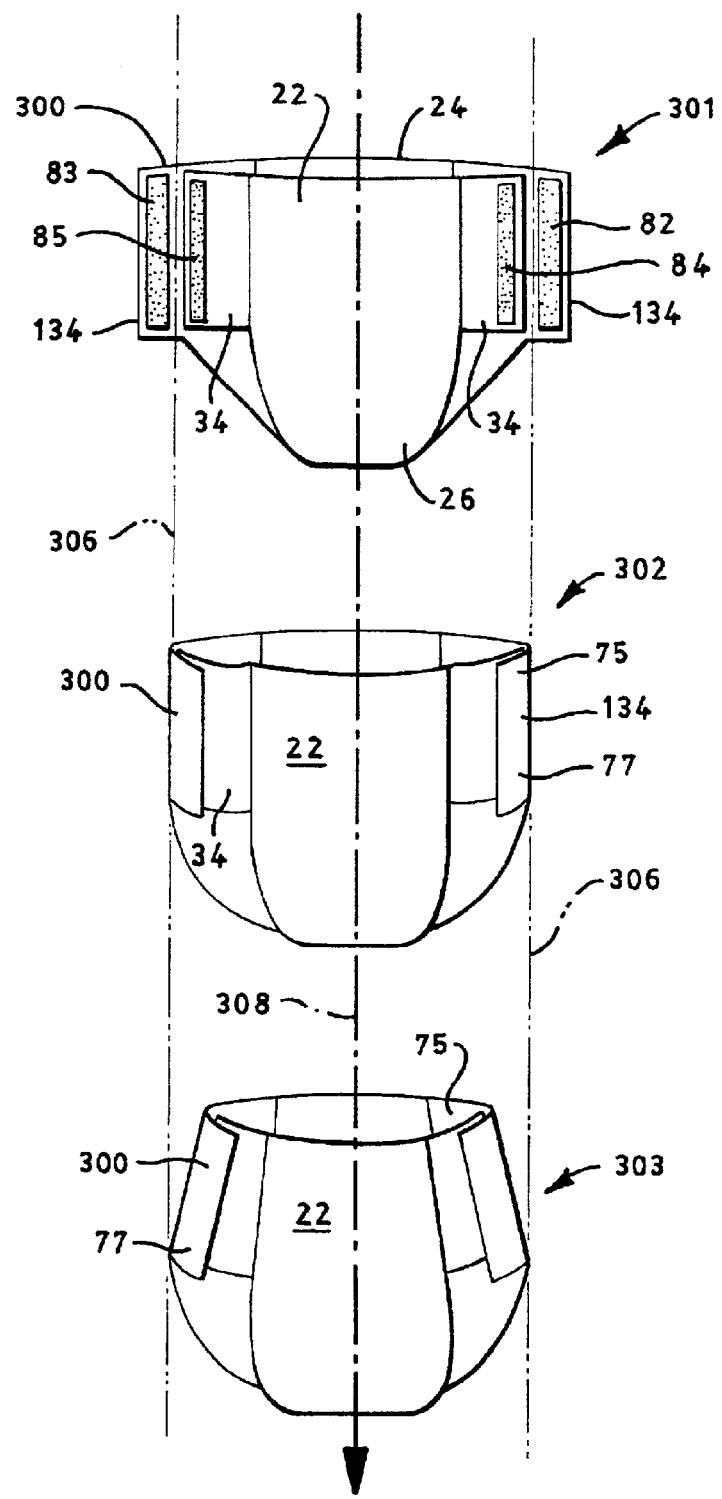
FIG. 5 illustrates a pant according to the present invention at three stages during manufacture.

FIG. 5 illustrates a training pant 300 at three stages during manufacture, denoted with reference numerals 301, 302 and 303. The training pant 300 is similar to the training pant 20 shown in FIG. 1, although the front side panels 34 are narrower than the back side panels 134. The training pant 300 at stage 301 has been folded through the crotch region 26 to overlap the waist regions 22 and 24 and the hip regions. At stage 302, one or both pairs of side panels 34 and 134 of the training pant 300 can be folded along fold lines 306 which are parallel to the longitudinal centerline 308 of the training pant. With the fastening components 82–85 engaged, the waist regions 22 and 24 define the waistband 75 and hip section 77, both of which encircle the pant 300 between the crotch region 26 and the waist opening. The waistband 75 is contiguous with the waist opening 50 (FIG. 1) while the hip section 77 is disposed between the waistband and the leg openings 52 (FIG. 1). At stage 303, the retractive materials forming the waist elastic members 54 and 56, the side panels 34 and 134, and/or other components can be activated and the retractive materials allowed to retract. Retraction causes the pant 300 to have the desired WHCR.

Figure 6:
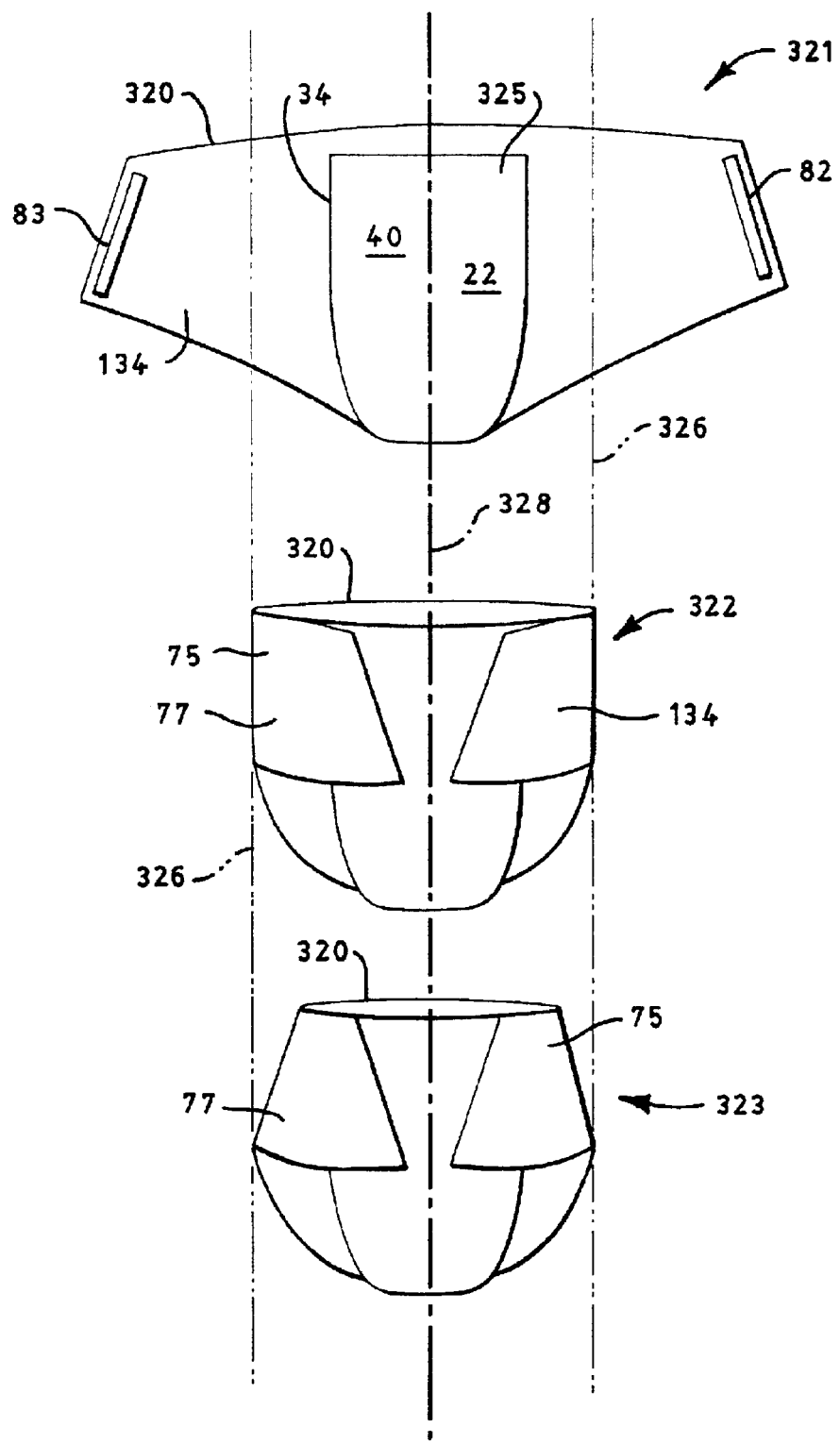
FIG. 6 illustrates an alternative pant according to the present invention at three stages during manufacture.

FIG. 6 illustrates an alternative pant 320 at three stages during manufacture, denoted with reference numerals 321, 322 and 323. The pant 320 of this embodiment comprises integral back side panels 134 and first fastening components 82–83 oriented at an angle relative to the longitudinal centerline 328 of the training pant. The second fastening components 325 can comprise a portion or portions of the outer cover 40 or the front side panels 34. The stages 321–333 are similar to those described in relation to FIG. 5. Despite the first fastening components 82–83 being oriented at an angle relative to the longitudinal centerline 328, the manufacturing process is significantly simplified by folding the back side panels 134 along fold lines 326 which are parallel to the longitudinal centerline 328. The training pant 320 is illustrated at stage 323 after activation and retraction of the retractive materials with the desired WHCR.

Figure 10:
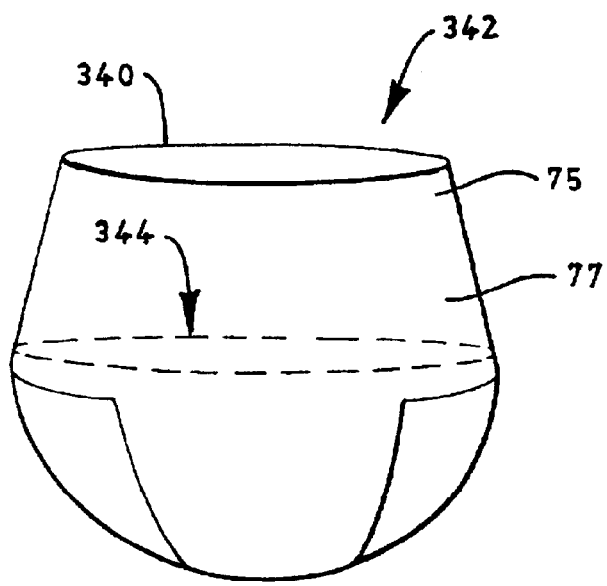
FIGS. 10 and 11 schematically illustrate pants in an unstretched condition and a fully stretched condition, respectively.
Figure 11:
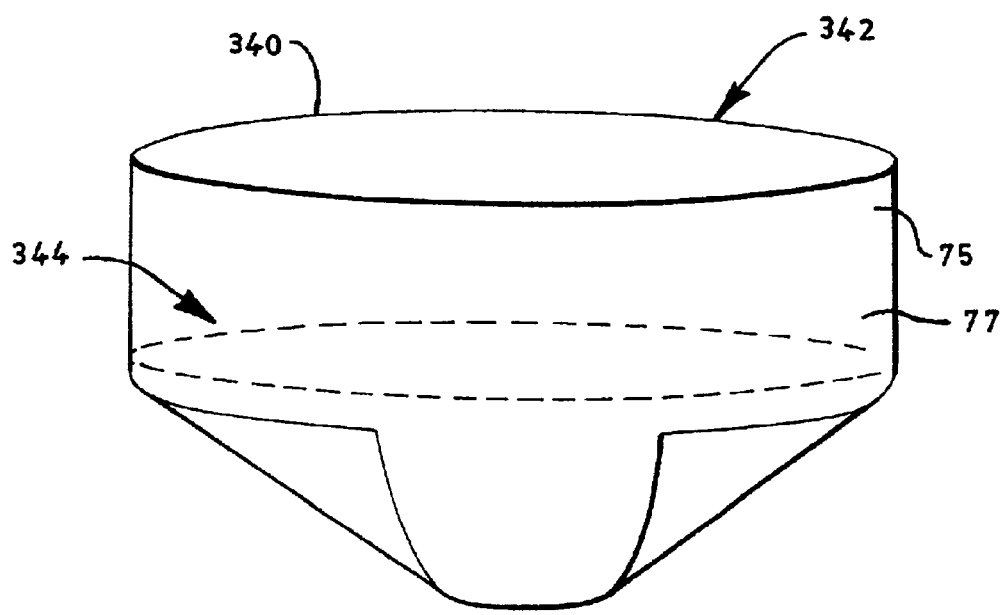

FIGS. 10 and 11 schematically illustrate a training pant 340 in an unstretched condition and a fully stretched condition, respectively. In the unstretched condition, (FIG. 10), the circumference of the waistband 75, which is denoted at arrow 342, is smaller than the circumference of the hip section 77, which is denoted at arrow 344, to provide the desired WHCR. When the training pant 340 is stretched to a maximum point, for example, about 2000 grams (FIG. 11), the waistband circumference 342 can but need not necessarily be substantially equal to the hip circumference 344.

Waistband-to-Hip Circumference Ratio WHCR Procedure

This procedure is a single-cycle tension bench test to measure waistband and hip circumferences of a test pant. The procedure measures waistband and hip circumferences under a minimum tension and also under a maximum tension. A test pant is cycled to a specific loading rather than to a fixed elongation/extension.

Data generated by this test method includes:

Waistband circumference (mm) at an initial load of 70 g.

Waistband circumference (mm) at a final (peak) load of 2000 g.

Hip circumference (mm) at an initial load of 70 g.

Hip circumference (mm) at a final (peak) load of 2000 g.

1. Overview

Figure 8:
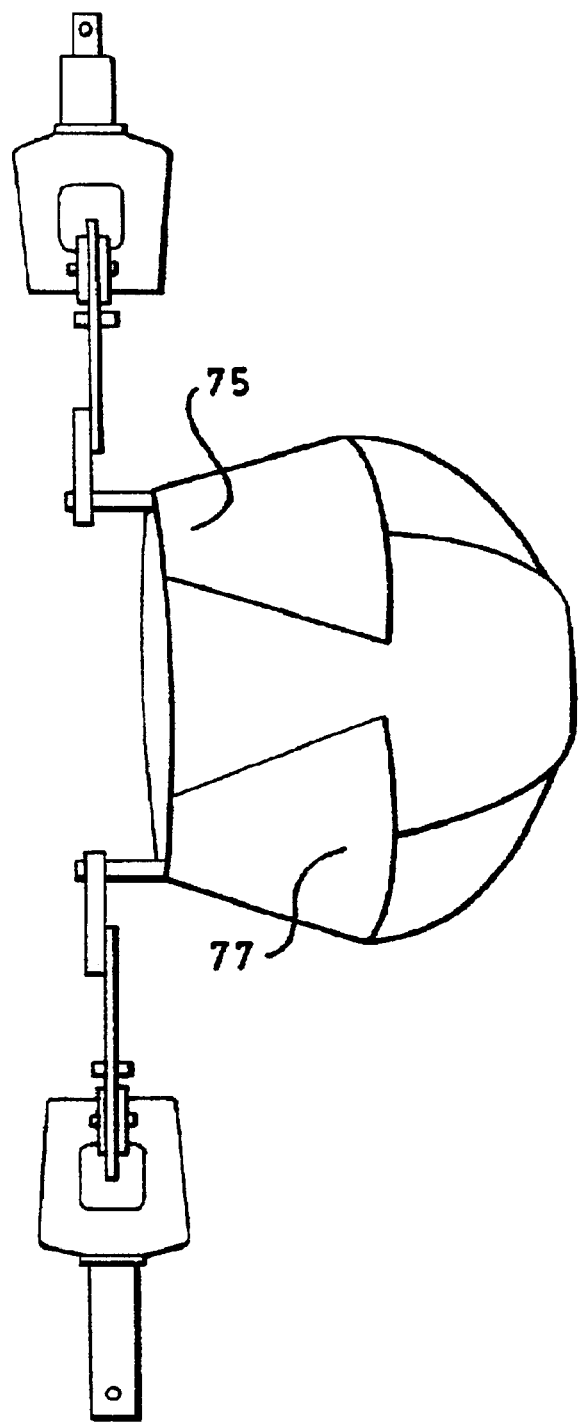
FIG. 8 illustrates a pant of the type shown in FIG. 6 disposed on the tensile tester to measure the waistband circumference.

A pant is placed on the upper and lower pins in position to measure the waistband gage length, as shown in FIG. 8. The gage length is selected for the waist opening of the pant being tested, so as to provide a tension of between 0 and 65 grams (g) when the pant is positioned for the test, prior to the start of the test. The term "tension" refers to the gram value measured by the load cells in the tensile tester.

The jaws are separated until a load of 70 grams of tension is attained, at which tension the gage length is recorded. Then the jaws continue to move apart until 2,000 grams of tension is reached, at which tension the gage length is again recorded. The standard test is one cycle per pant, although more can be used, and extension and tension data can be collected at 25 gram tension increments if desired. The circumference at a given tension may be calculated using the gage length and the circumference value(s) for the upper and lower pins. Desirably at least 3 pants are tested. The waistband circumference values at 70 grams tension from each pant tested are averaged to obtain an average initial waistband circumference, and the waistband circumference values at 2,000 grams tension from each pant tested are averaged to obtain an average final waistband circumference.

Figure 9:
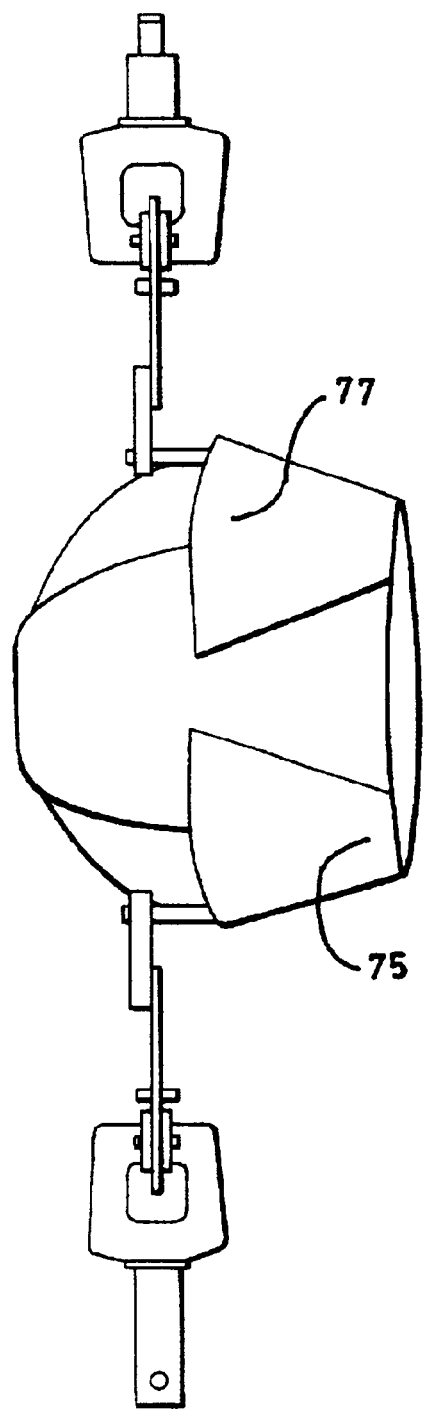
FIG. 9 illustrates a pant of the type shown in FIG. 6 disposed on the tensile tester to measure the hip circumference.

The procedure is repeated except that a fresh sample pant is placed on the upper and lower pins in position to measure values for the hip gage length, as shown in FIG. 9. As with the waistband gage length, the standard test is one cycle per pant, although more can be used. Desirably at least 3 pants are tested. The hip circumference values at 70 grams tension from each pant tested are averaged to obtain an average initial hip circumference, and the hip circumference values at 2,000 grams tension from each pant tested are averaged to obtain an average final hip circumference. The sample products being tested can be randomized and separate samples are used to test each product parameter, thus eliminating position interactions.

Figure 7:
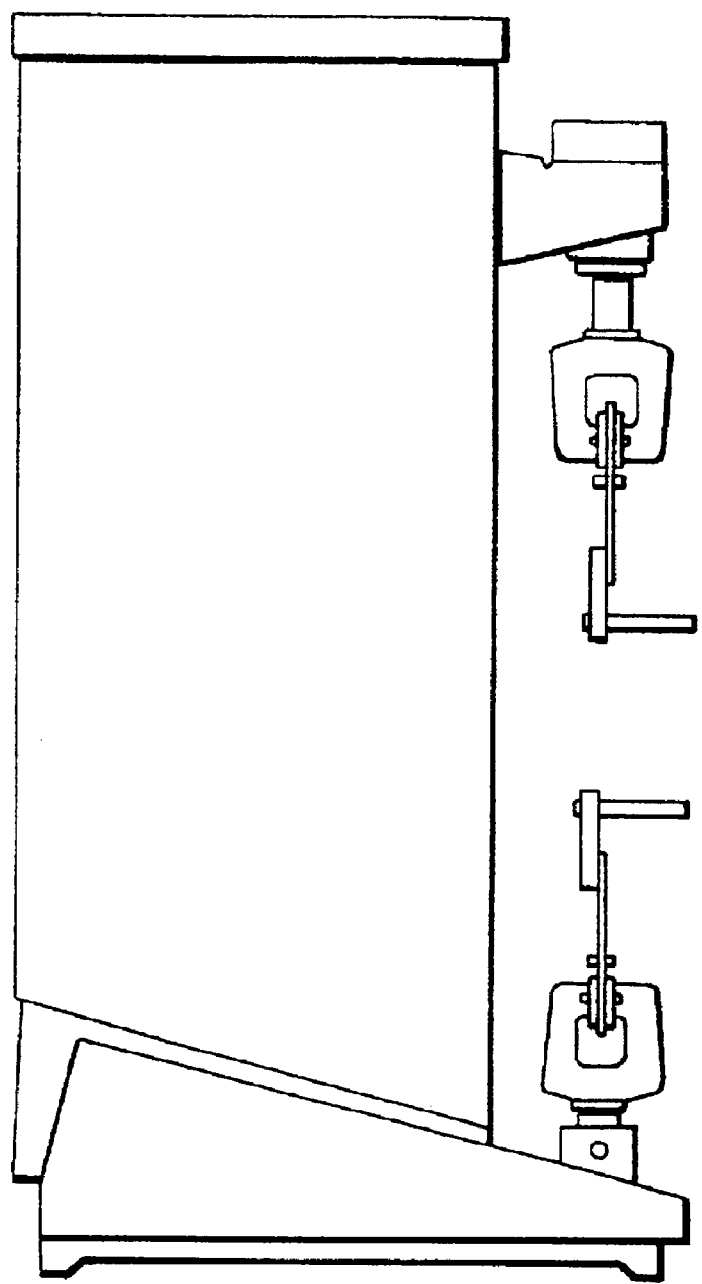
FIG. 7 illustrates a side view of a tensile tester used to measure waistband-to-hip circumference ratio of the pants shown in FIGS. 1, 5 and 6.

The waistband-to-hip circumference ratio of the pant at a given loading (tension level) is the average waist circumference at that loading divided by the average hip circumference at the same loading. FIG. 7 illustrates a side view of a tensile tester used to measure waistband-to-hip circumference ratios of pants according to the present invention. FIG. 8 illustrates a pant of the type shown in FIG. 6 disposed on the tensile tester to measure the waistband circumference. FIG. 9 illustrates a pant of the type shown in FIG. 6 disposed on the tensile tester to measure the hip circumference.

2. Apparatus and Materials
   2.1 Constant Rate of Extension (CRE) tensile tester: MTS tensile tester model Synergie 200 Test Bed; available from MTS® Systems Corporation, Research Triangle Park, N.C. USA.
   2.2 Load cells: A suitable cell selected so the majority of the peak load values fall between the manufacturer's recommended ranges of load cell's full scale value; Model 100N available from MTS® Systems Corporation, Research Triangle Park, N.C. USA.
   2.3 Operating software and data acquisition system: MTS TestWorks® for Windows software version 3.10; available from MTS® Systems Corporation, Research Triangle Park, N.C. USA.
   2.4 Grips: pneumatic-action grips, top and bottom, identified as part number 2712-003 available from Instron Corporation, Canton, Mass. USA.
   2.5 Grip faces: 25 by 75-mm (1 by 3-inch), suitable for holding pins.
   2.6 Pins: rigid pins having a length of 6.3 centimeters (2.5 inch) and a knurled portion at one end for holding specimens, the knurled portion having an outside diameter of 6.4 millimeter (0.25 inch) and a length of 3.2 centimeters (1.25 inch).
   2.7 Clips: 1.9 cm. wide by 0.95 cm. capacity (¾" wide by ⅜" capacity) binder clips; part no. BTM00251 available from BT Office Products, Milwaukee, Wis., USA.
3. Conditioning
   Conduct test in standard ASTM laboratory conditions: atmosphere of 23±2° C. (73.4±3.6° F.) and 50±5% relative humidity. The products should be measured after they equilibrate to laboratory conditions.
4. Test Specimen
   No preparation needed. The whole pant is tested.

5. Procedure

Tensile Tester test conditions:

| | |
|---|---|
| Cross head speed: | 250 mm/min |
| Full scale load: | 4540 g |
| Gage length: | Appropriate starting gage length settings for both hip and waistband are those that will generate initial loads of between 0 and 65 g in a previously untested product |
| Go to load (cycle trigger): | 2000 g (or a maximum load value that can be experienced by the sample without causing the sample to tear or otherwise come apart) |
| Number of cycles: | 1 |
| Elongation stop: | 450 mm (200%) |
| Break sensitivity: | 75% |

A. Install pin assemblies as depicted in FIG. 7.
B. Using the tensile frame pushbutton controls for crosshead position, move pins so that the pant can be mounted on the pins without stretching the pant. Determine the gage length by measuring from the centerline of the first pin to the centerline of the second pin. Calibrate the software to this initial gage length.
C. Place the waistband onto the knurled section of the top pin. Center one side of the pant on top of the pin. Use a single binder clip to hold the pant at the waist opening in place on the pin; do not stretch the pant during application of the clip.
D. Click on ZERO to tare the load of the pant. Only tare the weight of the first pant for each sample population, not for each specimen.
E. Place the waistband on the opposite side of the pant on the bottom pin and clip in place as for the first pin. Adjust pant so both top and bottom pins are inserted 2.5 centimeters (1 inch) into the pant.
F. Using the tensile frame pushbutton controls for crosshead position, move pins apart until the load applied to the waistband is between 0 and 65 g.
G. Click on RUN button. The test will start automatically.
H. When the test is done, click on either FILE to save the data and graphs or NEXT to save only the data.
I. Remove the sample from the pins.
J. Repeat steps B, C and E through I for each waist specimen until the testing is complete.
K. Using the tensile frame pushbutton controls for crosshead position, move pins toward one another so that the pant can be mounted on the pins without stretching the pant.
L. Place the hip section of a fresh sample (not used for waistband testing) onto the knurled section of the top pin. Center one side of the pant on the top of the pin. Use a single binder clip to hold the pant in place on the pin; do not stretch the pant during application of the clip.
M. Click on ZERO to the tare the load of the pant. Only tare the weight of the first pant for each sample population, not for each specimen.
N. Place the hip section on the opposite side of the pant on the bottom pin and clip in place as for the first pin. Adjust pant so both top and bottom pins are inserted 2.5 centimeters (1 inch) into the pant.
O. Using the tensile frame pushbutton controls for crosshead position, move pins apart until the load applied to the hip section is between 0 and 65 g.
P. Click on RUN button. The test will start automatically.
Q. When the test is done, click on either FILE to save the data and graphs or NEXT to save only the data.
R. Remove the sample from the pins.
S. Repeat steps K, L and N through R for each hip specimen until the testing is complete.

The circumference of a measured waistband or hip section at any tension may be calculated by multiplying the gage length at that tension by 2, and adding one half the circumference of the upper pin and one half the circumference of the lower pin. The waistband-to-hip circumference ratio is calculated by dividing the average circumference of the waistband at a given tension or load by the average circumference of the hip section at the same tension or load. At a load of 70 grams, for example, the WHCR for a pant is the average initial waistband circumference divided by the average initial hip circumference. Similarly, the WHCR for a pant at 2,000 grams is the average final waistband circumference divided by the average final hip circumference.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for making a prefastened and refastenable pant, comprising;

providing a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels;

providing an activatable retractive material in at least one of the waist regions;

folding each article through the crotch region;

folding the opposed side panels to overlap at least portions of the first and second fastening components;

engaging the first and second fastening components; and activating at least a portion of the refractive material causing the retractive material to retract subsequent to engagement of the fastening components, wherein activating the refractive material provides a waistband-to-hip circumference ratio of about 95 percent or less at a 70 gram loading and a waistband-to-hip circumference ratio of about 100 percent at a 2000 gram loading.

2. The process of claim 1, wherein activating the refractive material comprises applying electromagnetic radiation.

3. The process of claim 1, wherein activating the refractive material comprises applying heat.

4. The process of claim 3, wherein applying heat comprises applying a volume of heated air and a greater volume of heated air is applied to a waistband as compared to a hip section.

5. The process of claim 3, wherein applying heat comprises applying an air flow and a higher temperature air flow is applied to a waistband as compared to a hip section.

6. The process of claim 1, further comprising temporarily maintaining the retractive material in an extended and unstable state by application of a compaction force.

7. The process of claim 1, wherein activating the retractive material provides a waist-to-hip circumference ratio of about 90 percent or less.

8. The process of claim 7, wherein activating the retractive material provides a waistband-to-hip circumference ratio of about 75 to about 90 percent.

9. A process for making a prefastened and refastenable pant, comprising:

providing a plurality of discrete articles, each article having first and second waist regions, a crotch region interconnecting the waist regions, a longitudinal centerline, first and second fastening components disposed in the first and second waist regions respectively and adapted to refastenably engage one another, the first waist region having opposed side panels;

providing an activatable retractive material in at least one of the waist regions;

obtaining position control of the opposed side panels;

activating at least a portion of the retractive material causing retraction of the retractive material, wherein activating the retractive material provides a waistband-to-hip circumference ratio of about 95 percent or less at a 70 gram load and a waistband-to-hip circumference ratio of about 100 cement at a 2000 gram loading;

folding each article through the crotch region;

folding the opposed side panels to overlap at least portions of the first and second fastening components;

engaging the first and second fastening components; and maintaining position control of the opposed side panels until the fastening components are engaged.

10. The process of claim 9, wherein activating the retractive material comprises applying electromagnetic radiation.

11. The process of claim 9, wherein activating the retractive material comprises applying heat.

12. The process of claim 9, further comprising temporarily maintaining the retractive material in an extended and unstable state by application of a compaction force.

13. The process of claim 9, wherein at least a portion of the retractive material is activated prior to engaging the first and second fastening components.

14. The process of claim 13, wherein at least a portion of the retractive material is activated prior to folding the opposed side panels.

15. The process of claim 9, wherein activating the retractive material provides a waistband-to-hip circumference ratio of about 90 percent or less.

16. The process of claim 15, wherein activating the retractive material provides a waistband-to-hip circumference ratio of about 75 to about 90 percent.

* * * * *